(12) United States Patent
Popescu et al.

(10) Patent No.: US 10,256,262 B2
(45) Date of Patent: *Apr. 9, 2019

(54) SYSTEM AND METHOD FOR HILBERT PHASE IMAGING

(71) Applicants: Massachusetts Institute of Technology, Cambridge, MA (US); Hamamatsu Photonics K.K., Hamamatsu (JP)

(72) Inventors: Gabriel Popescu, Champaign, IL (US); Ramachandra Dasari, Shererville, IN (US); Michael Feld, Jamaica Plain, MA (US); Takahiro Ikeda, Hamamatsu (JP)

(73) Assignees: Massachusetts Institute of Technology, Cambridge, MA (US); Hamamatsu Photonics K.K., Hamamatsu (JP)

( * ) Notice: Subject to any disclaimer, the term of this patent is extended or adjusted under 35 U.S.C. 154(b) by 31 days.

This patent is subject to a terminal disclaimer.

(21) Appl. No.: 14/301,187

(22) Filed: Jun. 10, 2014

(65) Prior Publication Data
US 2014/0361148 A1 Dec. 11, 2014

Related U.S. Application Data

(62) Division of application No. 11/389,670, filed on Mar. 24, 2006, now Pat. No. 8,772,693.
(Continued)

(51) Int. Cl.
*H01L 27/146* (2006.01)
*G01N 15/14* (2006.01)
(Continued)

(52) U.S. Cl.
CPC ....... *H01L 27/14601* (2013.01); *G01N 15/10* (2013.01); *G01N 15/1475* (2013.01);
(Continued)

(58) Field of Classification Search
CPC .......... H01L 27/14601; G06K 9/00134; G01N 15/10; G01N 15/1475; G01N 2015/0073;
(Continued)

(56) References Cited

U.S. PATENT DOCUMENTS 4,596,145 A 6/1986 Smith et al.
4,694,434 A 9/1987 von Ramm et al.
(Continued)

FOREIGN PATENT DOCUMENTS

CN 1156101 C 6/2004
JP H07-318806 A 12/1995
(Continued)

OTHER PUBLICATIONS

Arnison et al., Using the Hilbert transform for 3D visualization of differential interference contrast microscope images. J Microsc. Jul. 2000;199(Pt 1):79-84.
(Continued)

*Primary Examiner* — Francis M Legasse, Jr.
(74) *Attorney, Agent, or Firm* — McCarter & English, LLP

(57) ABSTRACT

Hilbert phase microscopy (HPM) as an optical technique for measuring high transverse resolution quantitative phase images associated with optically transparent objects. Due to its single-shot nature, HPM is suitable for investigating rapid phenomena that take place in transparent structures such as biological cells. A preferred embodiment is used for measuring biological systems including measurements on red blood cells, while its ability to quantify dynamic processes on the millisecond scale, for example, can be illustrated with measurements on evaporating micron-size water droplets.

20 Claims, 12 Drawing Sheets

Related U.S. Application Data

(60) Provisional application No. 60/665,118, filed on Mar. 25, 2005.

(51) Int. Cl.
*G01N 21/45* (2006.01)
*G06K 9/00* (2006.01)
*G01N 15/10* (2006.01)
*G01N 33/49* (2006.01)
*G01N 15/00* (2006.01)

(52) U.S. Cl.
CPC .......... *G01N 21/453* (2013.01); *G01N 33/49* (2013.01); *G06K 9/00134* (2013.01); *G01N 2015/008* (2013.01); *G01N 2015/0073* (2013.01); *G01N 2015/145* (2013.01); *G01N 2015/1454* (2013.01); *G01N 2015/1497* (2013.01)

(58) Field of Classification Search
CPC ....... G01N 2015/008; G01N 2015/145; G01N 2015/1454; G01N 2015/1497; G01N 21/453; G01N 33/49
See application file for complete search history.

(56) References Cited

U.S. PATENT DOCUMENTS

| | | | |
|---|---|---|---|
| 5,194,918 | A | 3/1993 | Kino et al. |
| 5,747,810 | A | 5/1998 | Schotland |
| 5,963,310 | A | 10/1999 | Brown et al. |
| 6,262,818 | B1 | 7/2001 | Cuche et al. |
| 6,456,380 | B1 | 9/2002 | Naganuma |
| 6,549,801 | B1 | 4/2003 | Chen et al. |
| 6,611,339 | B1 | 8/2003 | Yang et al. |
| 6,665,456 | B2 | 12/2003 | Dave et al. |
| 6,868,347 | B2 | 3/2005 | Li et al. |
| 8,772,693 | B2 | 7/2014 | Popescu et al. |
| 2002/0097402 | A1 | 7/2002 | Manning |
| 2002/0128544 | A1 | 9/2002 | Diab et al. |
| 2003/0227658 | A1 | 12/2003 | Thomas et al. |
| 2005/0046858 | A1* | 3/2005 | Hanson .............. G01B 11/0675 356/457 |
| 2005/0057756 | A1 | 3/2005 | Fang-Yen et al. |
| 2005/0105097 | A1 | 5/2005 | Fang-Yen et al. |
| 2005/0225769 | A1 | 10/2005 | Bankhead et al. |
| 2006/0103903 | A1 | 5/2006 | Thomas |
| 2006/0192969 | A1 | 8/2006 | Marks et al. |
| 2008/0032325 | A1 | 2/2008 | DiMarzio et al. |

FOREIGN PATENT DOCUMENTS

| | | |
|---|---|---|
| JP | 11-230833 A | 8/1999 |
| JP | 2002-526815 A | 8/2002 |
| WO | 00/20929 A1 | 4/2000 |
| WO | 03/078925 A2 | 9/2003 |

OTHER PUBLICATIONS

Belvaux et al., Visualization of Phase Objects by Hilbert Transformation. Nouvelle Revue d'Optique Appliquée, France. 1971;2(3):149-162.

Ikeda et al., Hilbert phase microscopy for investigating fast dynamics in transparent systems. Opt Lett. May 15, 2005;30(10):1165-7.

Kniffen et al., Bispectral magnitude and phase recovery using a wide bandwidth acousto-optic processor. Appl Opt. Mar. 10, 1992;31(8):1015-29.

Lowenthal et al., Observation of Phase Objects by Optically Processed Hilbert Transform. Appl. Phys. Lett. 1967;11(2):49-51.

Murphy et al., Interferometric interrogation of in-fiber Bragg grating sensors without mechanical path length scanning. Journal of Lightwave Technology. Jul. 2001;19(7):1004-1009.

Onodera et al., "A one-dimensional discrete Hilbert transform for interferometric phases," Advanced Materials and Devices for Sensing and Imaging II, Proceedings of SPIE, vol. 5633, pp. 256-263 (2005).

Popescu et al., Erythrocyte structure and dynamics quantified by Hilbert phase microscopy. J Biomed Opt. Nov.-Dec. 2005;10(6):060503.

Watanabe et al., Time-gated full-field optical coherence tomography using optical Hilbert transformation. The Second Asian and Pacific Rim Symposium on Biophotonics. APBP 2004. pp. 10-11.

Wikipedia. Digital holographic microscopy. Retrieved online at: https://en.wikipedia.org/wiki/Digital_holographic_microscopy#References. May 2017. 7 pages.

Wikipedia. Quantitative phase-contrast microscopy. retrieved online at: https://en.wikipedia.org/w/index.php?title=Quantitative_phase-contrast_microscopy?oldid=734365574. Aug. 2016 2 pages.

Third Party Observation for Application No. EP20100184686, dated Sep. 5, 2016.

* cited by examiner

SYSTEM AND METHOD FOR HILBERT PHASE IMAGING

CROSS REFERENCE TO RELATED APPLICATION

This application is a divisional application of U.S. application Ser. No. 11/389,670 filed Mar. 24, 2006 which claims priority to U.S. Provisional Application No. 60/665,118, filed Mar. 25, 2005, the entire contents of the above applications being incorporated herein by reference.

STATEMENT REGARDING FEDERALLY SPONSORED RESEARCH OR DEVELOPMENT

This invention was made with Government support under Grant No. RR002594 awarded by the National Institutes of Health. The Government has certain rights in this invention.

BACKGROUND OF THE INVENTION

Optical microscopy has been a commonly used method of investigation in medicine and biology. Numerous biological samples, including live cells, are quite transparent under visible light illumination and behave essentially as phase objects. Techniques such as phase contrast and Nomarski microscopy provide contrast of nearly invisible samples by transforming the phase information into intensity distribution and thus reveal structural details of biological systems. However, the information obtained with these techniques about the phase shift associated with the illuminating field is only qualitative. Retrieving quantitative phase information from transparent objects with high accuracy and low noise allows for measurements in the biological investigation of structure and dynamics. Both interferometric and non-interferometric techniques have been proposed for quantitative phase imaging of biological samples. Also Fourier phase microscopy (FPM) has been developed as an extremely low-noise phase imaging method. Due to the sub-nanometer phase stability over extended periods of time, FPM is suitable for investigating dynamics in biological systems on time scales from seconds to a cell lifetime.

SUMMARY OF THE INVENTION

Many processes that take place at the cellular level, including cytoskeletal dynamics, cell membrane fluctuations and neural activity occur at shorter time scales, down to the millisecond range. Therefore, a microscope that allows acquisition of full-field quantitative phase images at kHz frame rates enables quantification of biological systems.

The complex analytic signal formalism of time-varying fields has found broad applications in optics. In particular, the Hilbert transform relationship between the real and imaginary part of a complex analytic signal has been used to retrieve phase shifts from single temporal interferograms. The present invention relates to systems and methods for quantitative phase imaging, referred to as Hilbert phase microscopy (HPM), which allows the retrieval of a full field phase image from a single spatial interferogram.

In HPM, single-shot phase imaging is limited in frame acquisition rate only by the recording device such as an imaging sensor. Examples of imaging sensors include digital imaging detectors such as charge coupled devices (CCD) or a CMOS imaging array. This contrasts with phase-shifting techniques, in which multiple recordings are required for retrieving a single phase image. In addition, HPM provides for phase unwrapping, which enables the study of phase objects much larger than the wavelength of light. The imaging device preferably has at least 200,000 pixels that can collect at least 10 frames per second and preferably over 100 frames per second.

A preferred embodiment splits the light from a single light source along a reference path and a sample path. The light along the sample path is directed through the sample or object being measured and the light along the reference path is modulated by a modulating element such that when the light from the sample is combined with the modulated reference light that an interference pattern is produced that is detected by the imaging sensor. The modulating element can be a rotating mirror or a movable lens, for example. Preferred embodiments of the invention can include fiber optics to couple light onto the object such as tissue to be imaged. Lasers or other highly coherent light sources of different wavelengths can be used. A computer or other data processor or image processor can be connected to the output of the imaging device for processing of the image data. In a preferred embodiment, the data processor is programmed with a software program to process the image by first removing noise using a selected point in the field of view as a reference. The image then undergoes a Hilbert transform to obtain a processed image. A Fourier transform is performed on the interferogram followed by application of a filter to obtain filtered image data. This is followed by application of an inverse Fourier transform to obtain wrapped and unwrapped phase images. This provides quantitative phase images of the object of interest.

Preferred embodiments of the invention can include configurations of Hilbert phase imaging according to the invention in which the optical geometry is set up for transmissive or reflective imaging. In a preferred embodiment an inverted microscope geometry can be used with a beam splitter used to combine the reference and sample images. A reflective measurement can be performed by attaching a reflective material, such as polystyrene beads to a cell membrane. Coherent light can then be reflected off this material to obtain an interferogram. This can be used to measure mechanical properties of the membrane such as the shear modulus or the bending modulus. The procedures described herein can used in-vitro on human or mammalian tissue or fluid or in-vivo on the human eye of other tissues, for example.

The invention provides for non-biological applications as well as biological applications; for instance the invention can provide for studying the phase profile of an optical fiber and/or other transparent or semi-transparent objects or materials including crystalline structures.

DETAILED DESCRIPTION OF THE INVENTION

Figure 1:
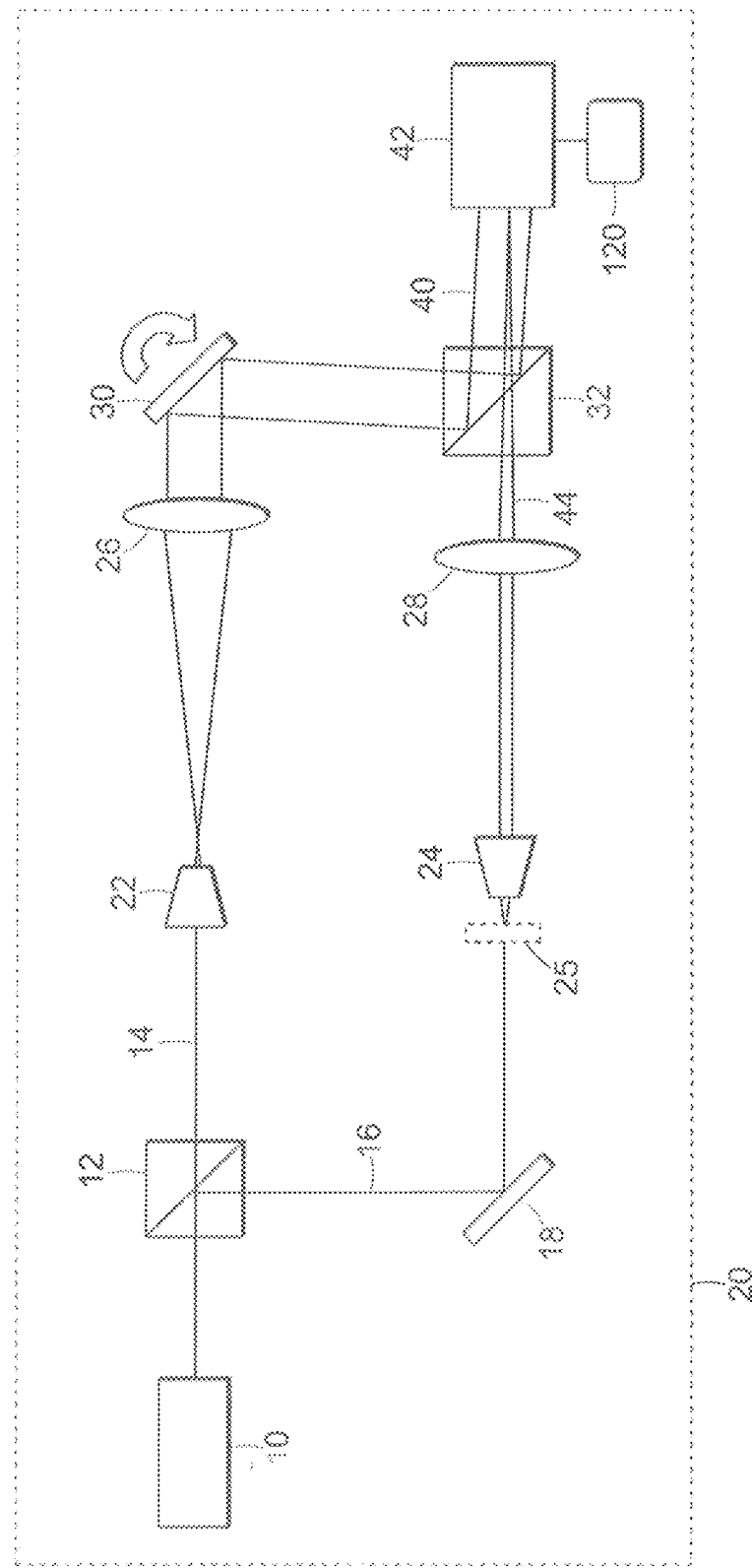
FIG. 1 illustrates a preferred embodiment of an imaging system in accordance with the invention.

A preferred embodiment of the invention is illustrated in FIG. 1. In this embodiment a HeNe laser is used as a light source 10 for an imaging Mach-Zender interferometer 20. A first beam splitter 12 splits the beam from the light source 10 to form two arms of the interferometer, the arms comprising a reference beam 14 and a sample beam 16, respectively. A mirror 18 directs the sample beam 16 onto a sample or object 25. In each arm of the interferometer 20 there are two telescopic systems, with magnification M=20 for example, each telescopic system comprises an objective 22, 24 and a lens 26, 28. A second mirror 30 directs the reference field onto a second beam splitter 32. The orientation of the reference field 40 is adjustable, for example, by rotatable movement of mirror 30 in order to tilt reference field 40. An image sensor 42, such as a CCD, can be positioned in the common Fourier plane of the lenses 26, 28 where the exact (magnified) replica of the sample field 44 is formed. The reference field 40, which is directed onto the CCD image sensor 42 by the beam splitter 32, is slightly tilted with respect to the sample beam 44 in order to create a uniform fringe structure oriented at 45° with respect to the x and y axes of the CCD image sensor 42. The CCD used in this embodiment (C770, Hamamatsu Photonics) has an acquisition rate of 291 frames/s at the full resolution of 480×640 pixels. Higher resolutions and acquisition rates can also be used. Image data is sent from the sensor 42 to the processor or computer 120 for analysis and display.

For a given sample 25, the spatially varying irradiance at the image plane across either the x or y axis has the form:

$$I(x) = I_R + I_S(x) + 2\sqrt{I_R I_S}(x)\cos[qx+\varphi(x)] \quad (1)$$

where $I_R$ and $I_S$ are, respectively, the reference and sample irradiance distributions, q is the spatial frequency of the fringes, and φ is the spatially varying phase associated with the object 25, the quantity of interest. Eq. (1) is analogous to describing the temporal interference in Michelson and other interferometers, in which q corresponds to the frequency shift introduced by an acousto-optic modulator or a moving mirror. For the transparent objects of interest here, $I_S(x)$ is expected to have a weak dependence on x. By adjusting the magnification of the system, the spatial frequency q can be chosen to match or exceed the maximum frequency allowed by the numerical aperture of the instrument, such that the diffraction-limited resolution is preserved. The sinusoidal term $u(x)=2\sqrt{I_R I_S}\cos[qx+\varphi(x)]$ can be isolated by Fourier high-pass filtering. It follows that the complex analytic signal, z(x), associated with the real function u(x) can be obtained as $$z(x) = \frac{1}{2}u(x) + i\frac{P}{2\pi}\int_{-\infty}^{\infty}\frac{u(x')}{x-x'}dx' \quad (2)$$

In Eq. 2, the imaginary part of the right hand side stands for a principle value (P) integral, identifiable as the Hilbert transform of u(x). Therefore, the phase spectrum, Φ(x), associated with the complex analytic signal, z(x), is calculated as $$\Phi(x)=\tan^{-1}\{Im[z](x)]/Re[z(x)]\} \quad (3)$$

Note that z(x) exhibits rapid phase modulation, with frequency q, and thus Φ is strongly wrapped. However, since q is higher than the spatial frequency content of the object, the unwrapping procedure works efficiently. Finally, the phase associated with the object, φ(x), is extracted simply as $$\varphi(x)=\Phi(x)-qx. \quad (4)$$

Figure 2A:
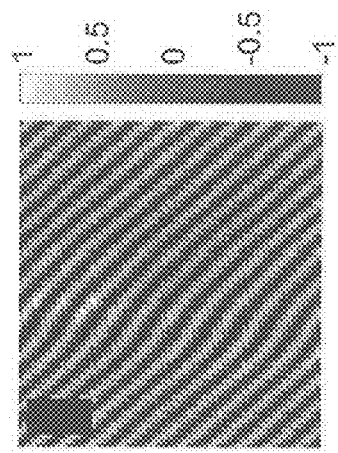
FIGS. 2a-2h illustrate images obtained including a) transmission intensity image; b) interferogram, c) sinusoidal signal, and d) wrapped phase measured from the rectangular area indicated in a); e) full-field unwrapped phase; f) full-field quantitative phase image; g) transverse profile through the phase image in f with the continuous line indicating the modeled fit; h) HPM image of a whole blood smear (magnification 40); the 5 μm scale bar is indicated; the gray scale bars indicate intensity levels for a-c, and phase in radians for d-h.
Figure 2B:
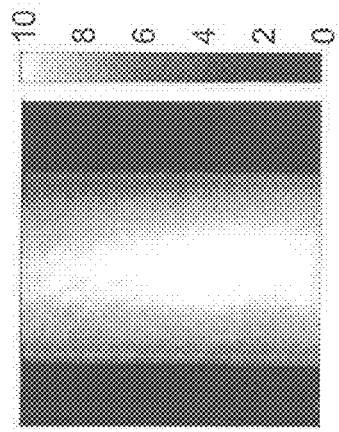
Figure 2C:
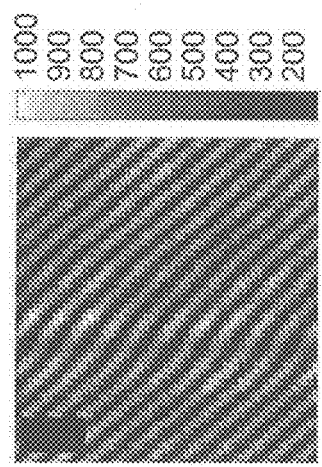
Figure 2D:
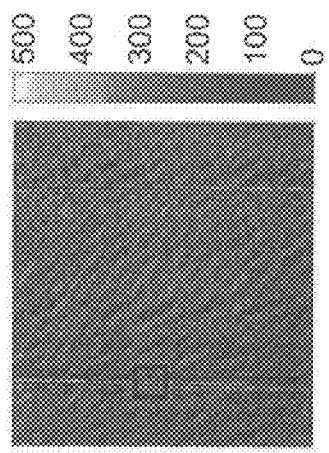
Figure 2E:
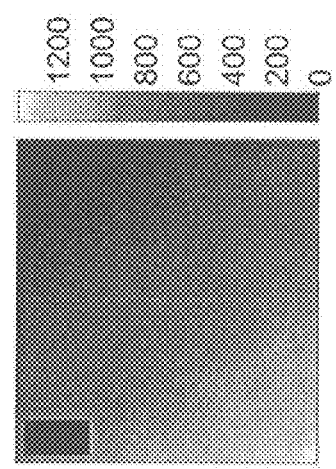
Figure 2F:
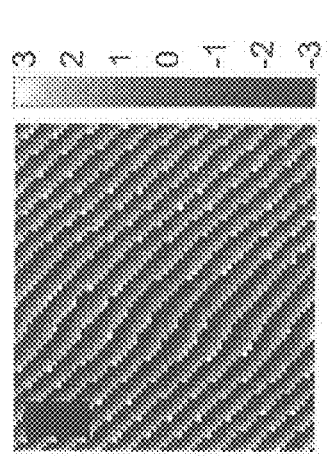
Figure 2G:
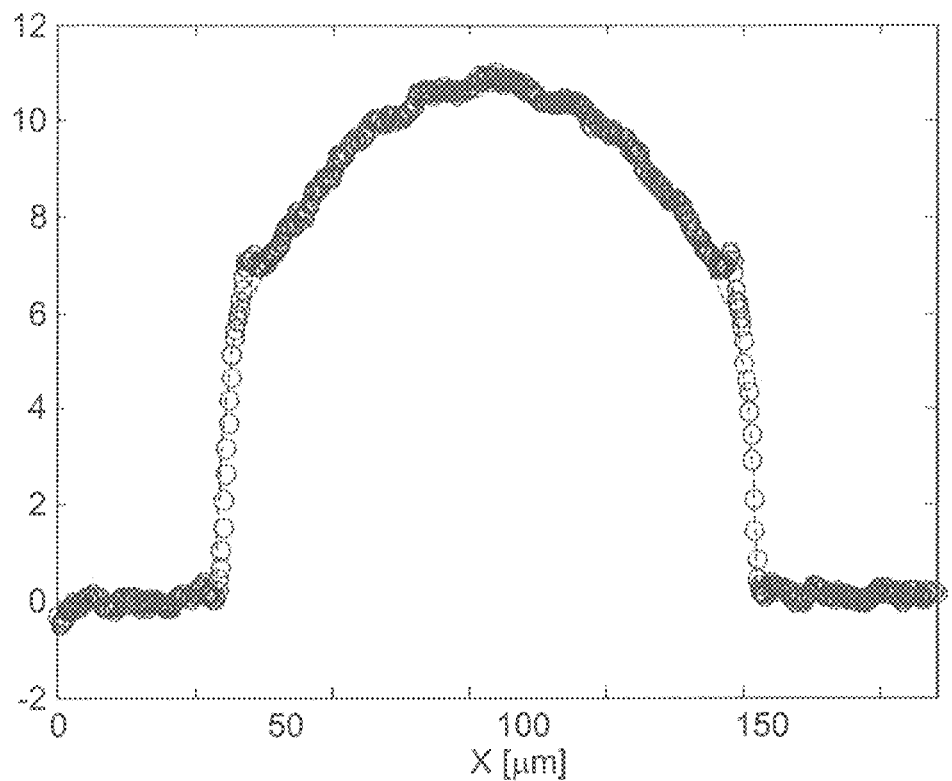

This procedure can be used to retrieve the phase profile of an optical fiber, for example. In a preferred embodiment, the invention provides for an apparatus and method for retrieving the phase profile of an optical fiber having a fiber core with a diameter of 100 μm and a refractive index of 1.457, while the cladding has an outer diameter of 110 μm and a refractive index of 1.452. The fiber is immersed in glycerol to better mimic a phase object, in this example. The transmission intensity image of this sample (FIG. 2a) shows low contrast, which is an indication of the transparency of the sample. FIGS. 2b-d represent intermediate steps in the phase reconstruction sequence and correspond to the rectangular area shown in FIG. 2a. This region encompasses the glycerol/cladding and cladding/core interfaces. The interferogram recorded by the CCD (FIG. 2b) is Fourier transformed and high-pass filtered, such that the sinusoidal signal is obtained (FIG. 2c). In order to obtain the complex analytic signal associated with this real signal, the 2D Fourier transform is computed and the negative spatial frequencies are suppressed. Upon the inverse Fourier transform operation a complex 2D signal is obtained that uniquely provides information about the phase of the object, as described in Eq. 2. The strongly wrapped and unwrapped phase images, respectively, are shown in FIGS. 2d and 2e. The quantitative phase image of the optical fiber is obtained by subtracting the linear phase and is depicted in FIG. 2f, while a cross-section is shown in FIG. 2g. The continuous line represents the modeled fit, with the refractive index of glycerol as the variable parameter. The refractive index of glycerol for the best fit has a value of n=1.467, which approximates known values.

Figure 2H:
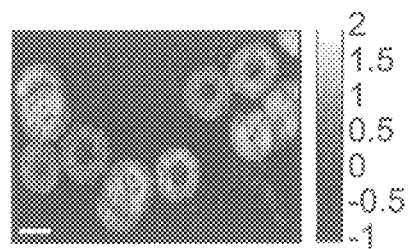

A preferred embodiment of the invention uses HPM for biological measurements, such as, for example, quantifying parameters for phase-images of tissue or body fluids such as red blood cells from whole blood smears. FIG. 2h shows an example of such an image, in which the individual cells and agglomeration of cells are easily identifiable. Red blood cells lack nuclei and major organelles can be modeled as optically homogeneous objects. Thus, the phase information from the HPM images can be transformed into thickness information, which directly provides parameters such as cell shape and volume. In this example, the data were recorded in 10.3 ms and the sample was prepared by sandwiching a droplet of whole blood between two cover slips.

Thus, according to preferred embodiments of the invention, HPM can provide quantitative phase images in transparent samples. In addition, this method can measure phase objects with phase profiles much higher than the wavelength of the illuminating light. This important feature is due to the high spatial modulation imposed on the image, which creates well defined wrapping points on the phase image, thus facilitating the unwrapping procedure. The ability of HPM to obtain quantitative phase images from single-shot measurements allows, therefore, monitoring fast dynamic processes in transparent or transmissive systems.

Figure 3B:
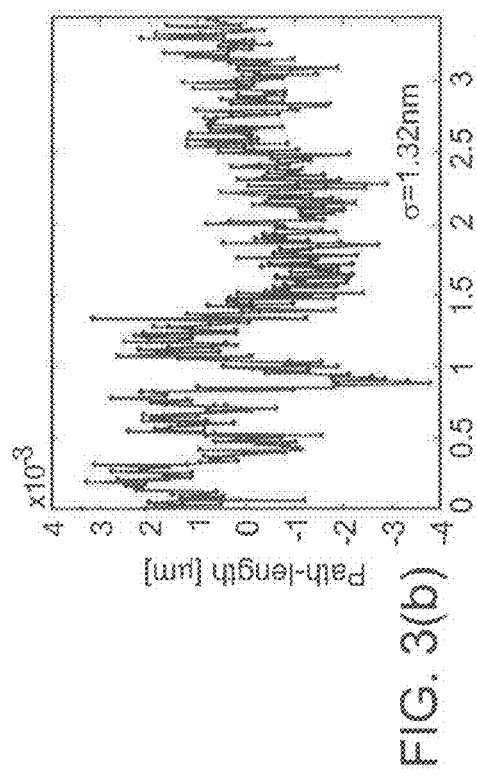
FIGS. 3a-3d are images obtained including a) HPM image of water droplets; the color bar indicates thickness in microns and the scale bar is 10 μm; b) path-length fluctuations of point O of FIG. 3a; the standard deviation is indicated; c) droplet mass (femto-gram units) temporal evolution during evaporation; d) maximum thickness of droplets during evaporation; with data being collected over a 3.4 s time interval, and with 10.3 ms between successive frames.
Figure 3D:
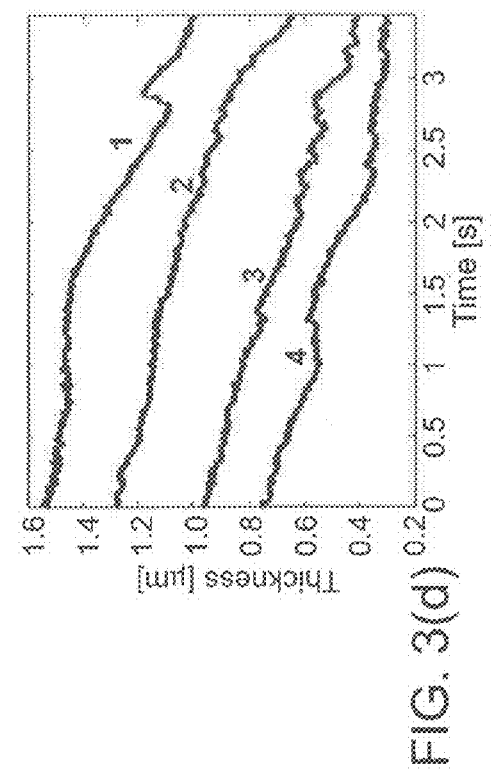
Figure 3A:
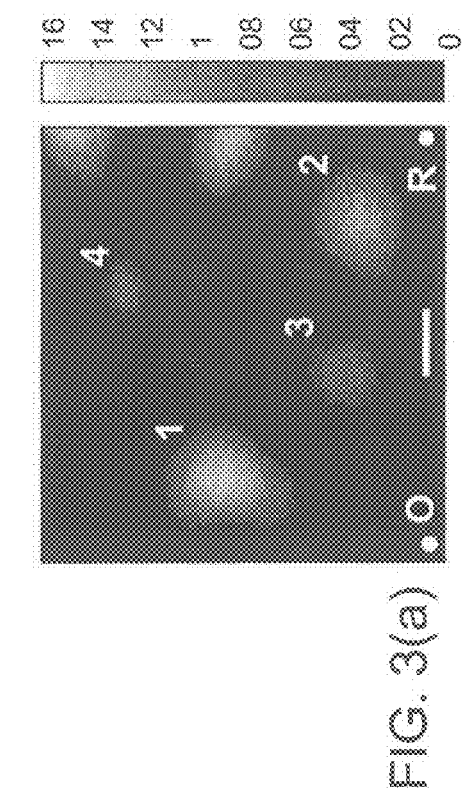
Figure 3C:
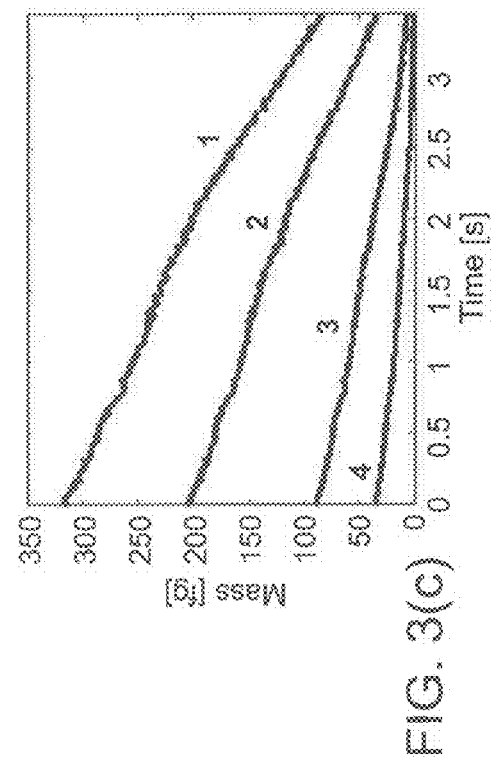

A further preferred embodiment of the invention provides for studying rapid processes in transparent media, such as, for example, analyzing the evaporation of micron-size liquid droplets. FIG. 3a shows the FPM image of such water droplets sprayed onto a microscope slide. The z-axis information indicates that the thickness of these droplets is significantly smaller than their transverse size. In order to monitor this evaporation phenomenon, a series of 333 phase images were recorded at time intervals of 10.3 ms. Since each phase image is obtained from one CCD recording, it is not necessary to eliminate noise between the two interferometer arms, which provides a significant advantage over phase-shifting techniques. The noise between successive frames does not obscure the phase images, which can be conveniently displayed by referencing each image to a fixed point in the field of view. This reference point is denoted in FIG. 2a by "R". In order to quantify the residual transverse noise present in the phase image series, temporal path-length fluctuations associated with point O indicated in FIG. 3a were recorded. These fluctuations were averaged over an area corresponding to the diffraction-limited spot of the imaging optics (0.45×0.45 µm²). The standard deviation of these fluctuations has a value of 1.32 nm, as shown, which indicates that nanometer path-length sensitivity can be obtained on the millisecond time scale. FIG. 3c shows the evolution of droplet masses during this recording, as calculated from the HPM images. For diffraction-limited transverse resolution and the current phase sensitivity, HPM is sensitive to water evaporation volumes that are remarkably small, on the order of $10^{-18}$ liters. In addition, the quantitative phase images offer detailed 3D information about these homogeneous structures. Thus, the temporal dependencies of the maximum thickness associated with the evaporating droplets can be easily estimated (FIG. 3d). These curves are significantly more irregular (sometimes non-monotonous) than the time evolution of the mass, which indicates the discontinuous nature of changes in shape during evaporation.

Preferred embodiments of the invention provide advantages. For instance, Hilbert phase microscopy according to the invention can retrieve high transverse resolution quantitative phase images from single-shot measurements with nanometer-level sensitivity. Applying complex analytic signals to the spatial domain is based on the analogy that exists between the equations describing the temporal and spatial fluctuations of electromagnetic fields. HPM provides a method for measuring rapid phenomena in transparent media, including the dynamics of biological systems and living cells.

Figure 4:
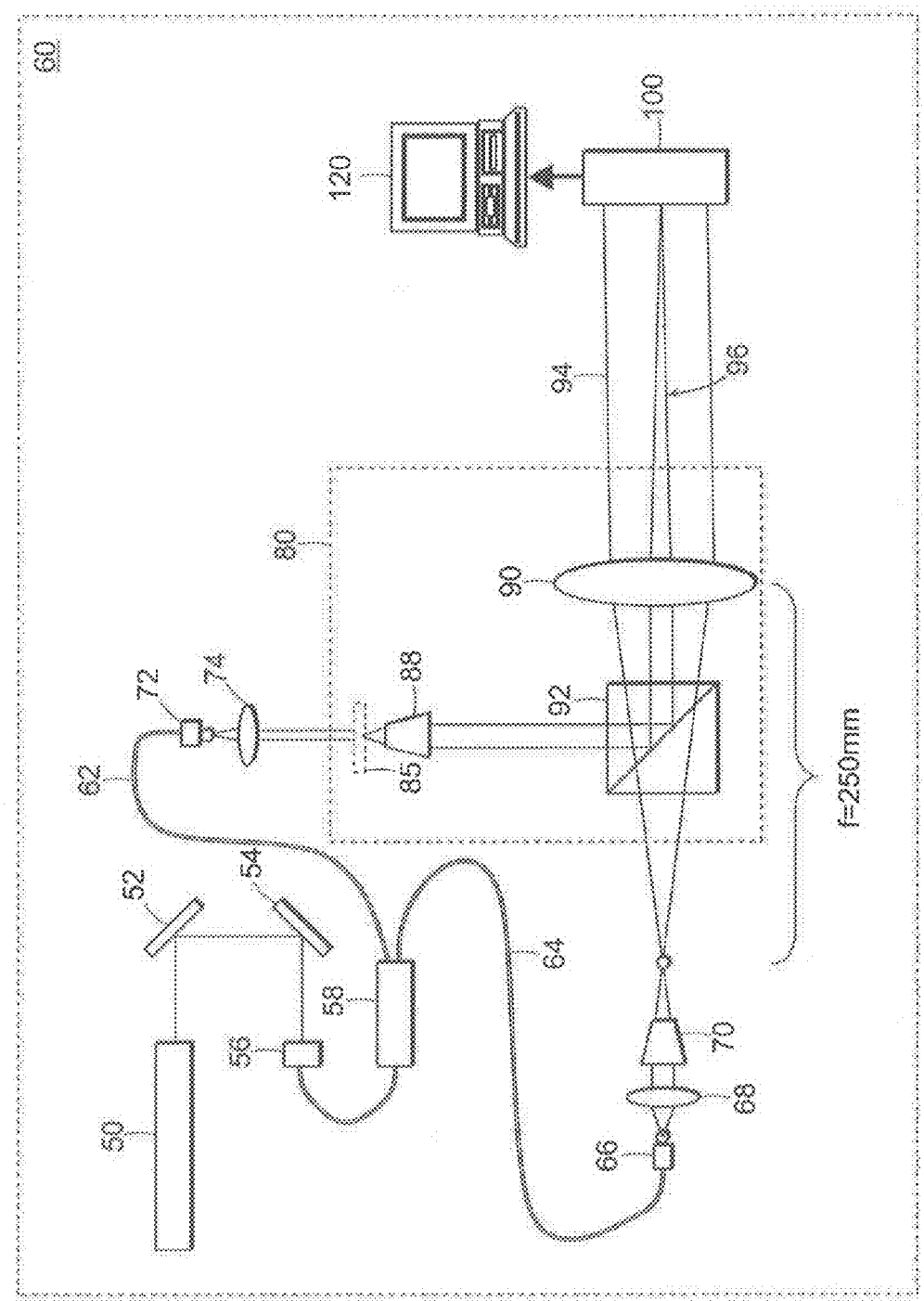
FIG. 4. illustrates a preferred embodiment of an imaging system in accordance with the invention.

Turning now to FIG. 4, a further preferred embodiment of the invention uses the principle of Hilbert phase microscopy in an inverted geometry to provide a high-speed and high-sensitivity quantitative phase microscope 60. The inverted geometry is particularly suitable for live cell investigation. The potential of the method for quantitative biological microscopy has been demonstrated by quantifying red blood cell shape and fluctuations with nanometer path-length sensitivity at the millisecond time scale.

Referring to FIG. 4, a preferred embodiment extends HPM by integrating it with an inverted microscope 60. A light source 50, such as, for example, a HeNe laser ($\lambda$=632 nm) is coupled by first mirror 52 and second mirror 54 into a 1×2 single-mode, fiber-optic coupler 56 and split through fiber splitter 58 to a reference arm 64, comprising a first fiber coupler output 66 and collimator 68, and to a sample arm 62, comprising a second fiber coupler output 72 and collimator 74. The first output field provided through the sample arm acts as the illumination field for an inverted microscope 80 equipped with a 100× objective 88. The tube lens 90 is such that the image of the sample 85 is formed at the plane of the image sensor CCD 100 via the beam splitter cube 92. The second fiber coupler output 66 is collimated by collimator 68 and expanded by a telescopic system consisting of second microscope objective 70 and the tube lens 90. This reference field beam can be approximated by a plane wave, which interferes with the sample image field 96. The reference field 94 is tilted with respect to the sample field 96 (for example, by adjusting collimator 68), such that uniform fringes are created at an angle of 45° with respect to x and y axes of the CCD 100. The CCD used (C7770, Hamamatsu Photonics) has an acquisition rate of 291 frames/s at the full resolution of 640×480 pixels and the CCD 100 can be connected to and controlled by computer 120. In this example, the focal distance, f, between the focus of the reference arm objective 3 and the tube lens 90 is 250 mm.

The spatial irradiance associated with the interferogram across one direction is given by Eq. 1, above, where $I_R$ and $I_S(x)$ are, respectively, the reference and sample irradiance distributions, q is the spatial frequency of the fringes, and $\varphi(x)$ is the spatially varying phase associated with the object 85, $\varphi(x)$ being an important quantity of interest in the analysis. Using high-pass spatial filtering to isolate the sinusoidal term $u(x)=2\sqrt{I_R I_S} \cos[qx+\varphi(x)]$, as described above, and applying the Hilbert transformation as in Eq. 2 above to obtain the complex analytical signal, z(x), (and thereby the phase spectrum $\Phi(x)$ through Eq. 3), again, by Eq. 4, the quantity $\varphi(x)$ can be retrieved for each point of the single-exposure image.

Figure 5A:
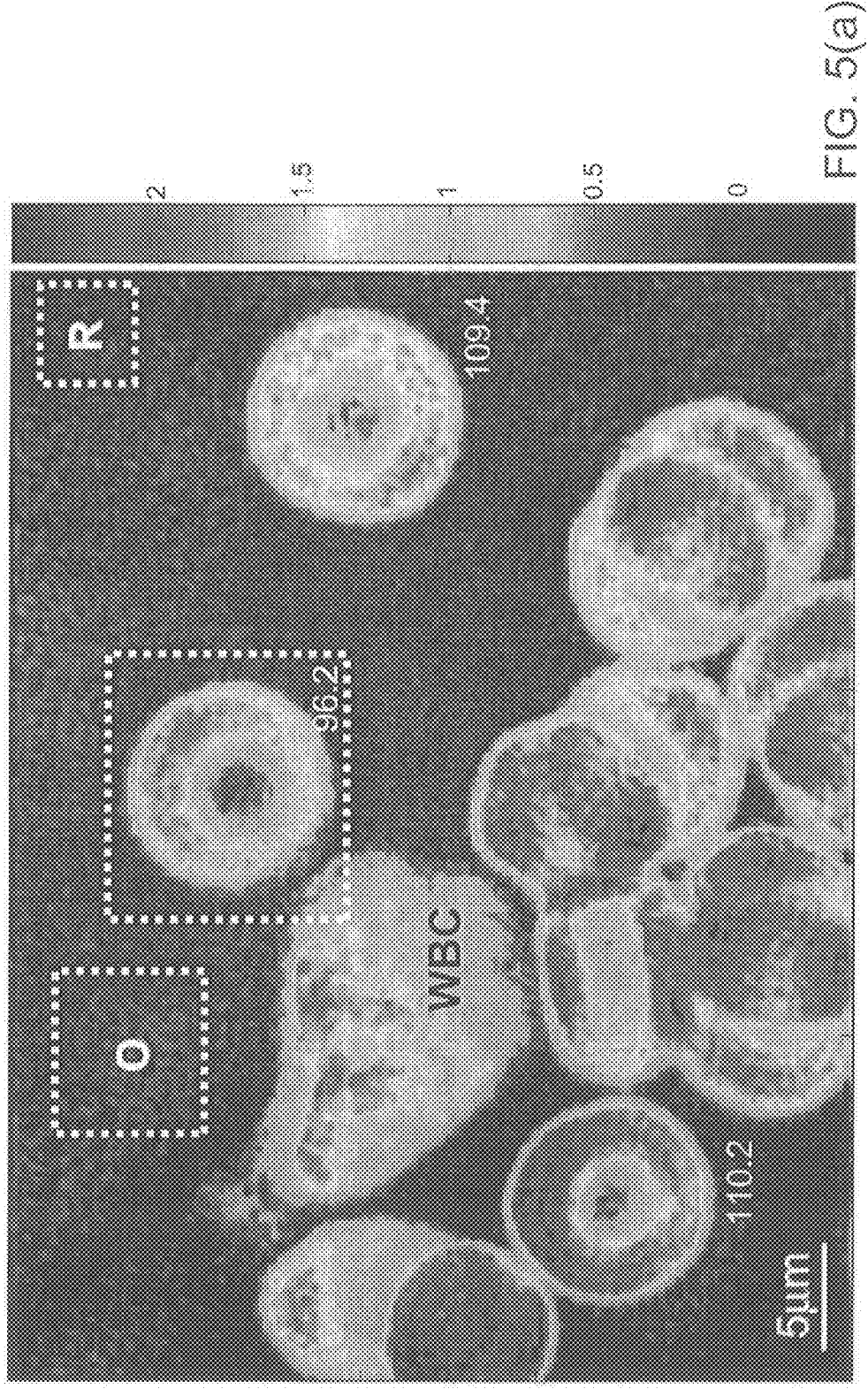
FIGS. 5a-5c illustrate images and data obtained including a) Quantitative phase image of whole blood smear; the volumes of RBCs (red blood cells) are indicated in femto-liters and the colorbar is in radians, and b) Temporal fluctuations of the spatial standard deviation associated with area O, and c) temporal average sigma.sub.s as function of averaging frames.
Figure 5B:
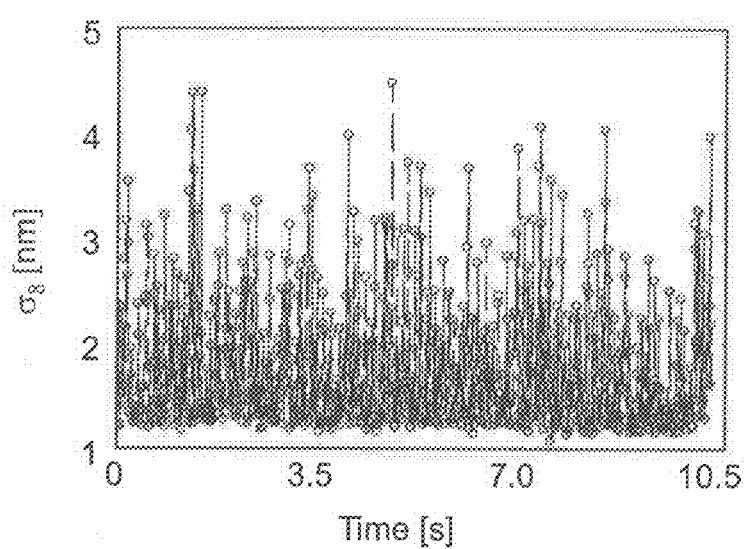

Owing to the inverted geometry, the new HPM microscope is particularly suited for the quantitative investigation of live cells. To demonstrate the ability of the new instrument to quantify cellular structures at the millisecond and nanometer scales, time-resolved HPM images of red blood cells (RBCs) were obtained. Droplets of whole blood were sandwiched between cover slips, with no additional preparation. FIG. 5 shows a quantitative phase image of live blood cells; both isolated and agglomerated erythrocytes are easily identifiable. A white blood cell (WBC) is also present in the field of view. Using the refractive index of the cell and surrounding plasma of 1.40 and 1.34, respectively, the phase information associated with the RBCs can be easily translated into a nanometer scale image of the cell topography. In addition, the volume of individual cells can be evaluated; in FIG. 5, the measured volumes (units of in femtoliters) are displayed below individual red blood cells.

Figure 5C:
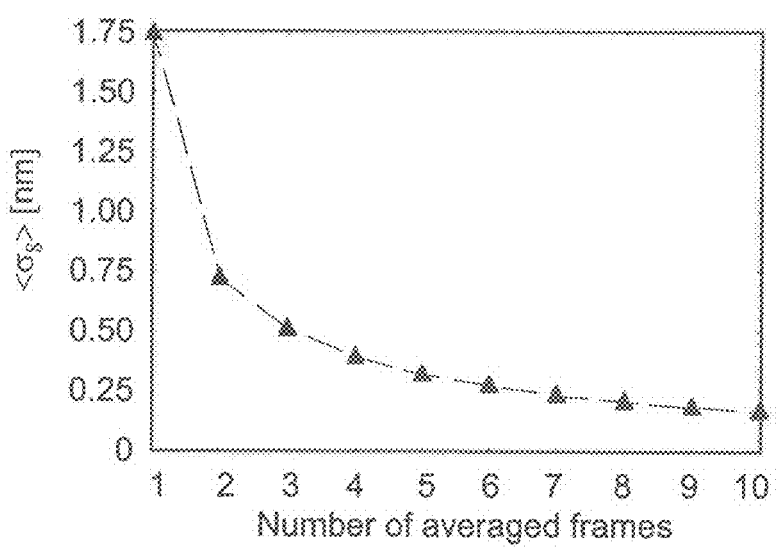

In order to eliminate the longitudinal noise between successive frames, each phase image was referenced to the average value across the area in the field of view containing no cells, denoted by R. To quantify the stability of the instrument and thus the sensitivity to dynamical changes of cell topography, sets of 1000 images were recorded, acquired at 10.3 ms each and noise analysis was performed on a second empty region in the field of view. The spatial standard deviation, $\sigma_s$, of the pathlength fluctuation across this area (indicated in FIG. 5a as O) has a certain fluctuation in time and is characterized in turn by a temporal average $<\rho_s>$. The time-dependence of $\sigma_s$ is plotted in FIG. 5b, while the mean value $<\sigma_s>$ versus the number of averaging frames is shown in FIG. 5c. Remarkably, $<\sigma_s>$ is lowered to less than 1 nm values by averaging only 2 successive frames. This noise assessment demonstrates that the inverted HPM instrument according to a preferred embodiment of the invention is capable of providing quantitative information about structure and dynamics of biological systems, such as RBCs, at the sub-nanometer scale.

Figure 6B:
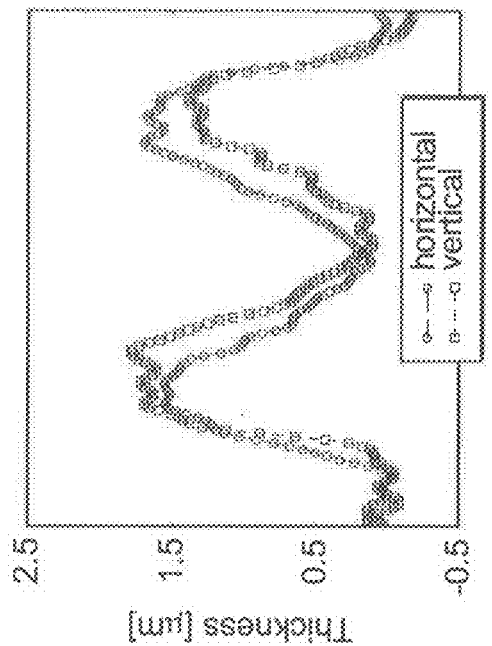
FIGS. 6a-6d illustrates quantitative assessment of the shape transformation associated with a red blood cell during a 10 second period.
Figure 6A:
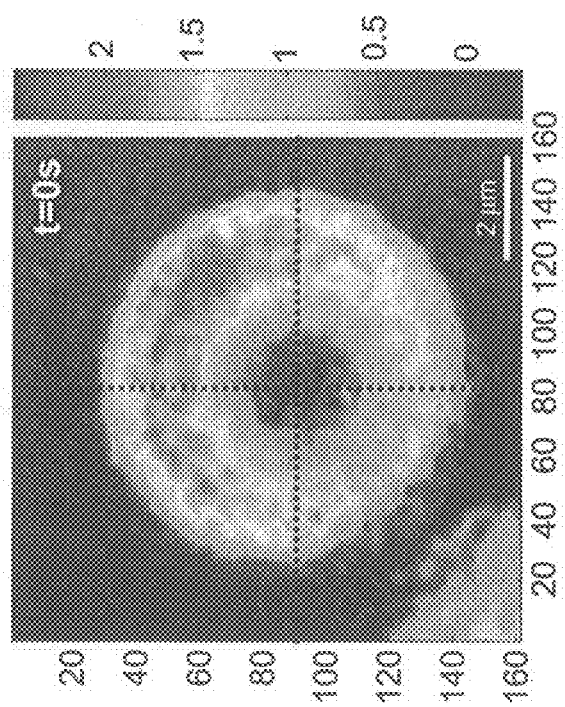
Figure 6D:
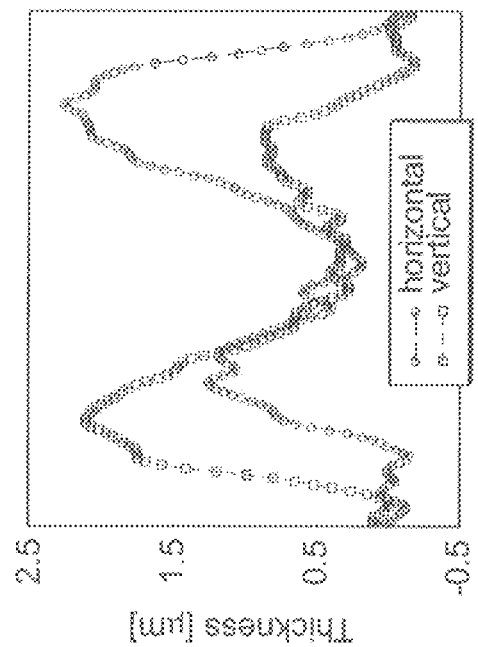
Figure 6C:
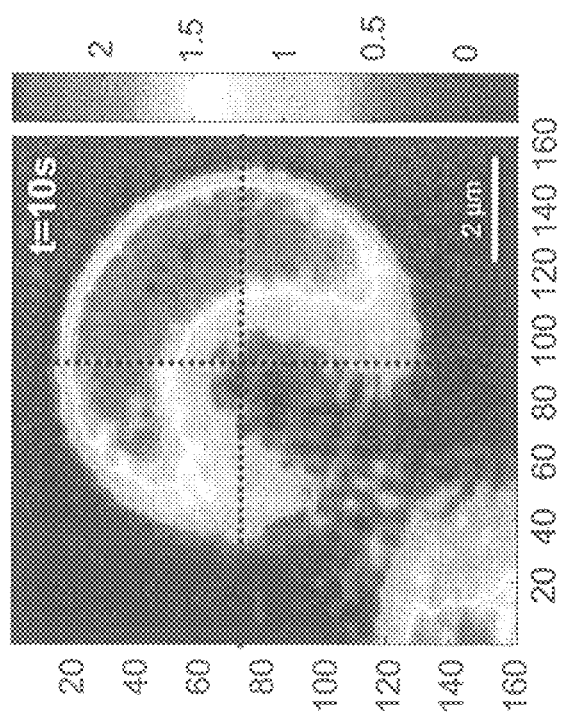

An example of significant dynamical change of a live red blood cell is shown in FIGS. 6a and 6c. The phase images correspond to the red blood cell shown in FIG. 5a and are acquired 10.3 ms apart and represent the first and the last frames in a 1,000 frame data set. FIGS. 6b and 6d show the horizontal and vertical thickness profiles of the cell at the two stages, with nanometer accuracy. Interestingly, the significant change in the cell shape is due to a rapid interaction with the neighboring white blood cell, at the lower left corner of the image (also shown as WBC in FIG. 5a). This results in a rapid asymmetric shape change that is easily quantified by HPM. This remarkable result cannot be quantified by techniques such as atomic force or electron microscopy.

Figure 7A:
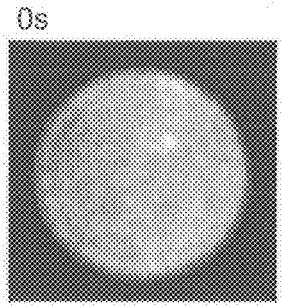
FIGS. 7a-7i illustrate images and data obtained including a-e) various stages of hemolysis during a 4 second period, and f-h) phase images of hemoglobin expelled from the cell corresponding to t=0.5 s, 1.0 s and 1.5 s, as indicated, and i) cell volume change and optical path-length shift associated with a point outside the cell (indicated by the arrow in FIG. 7f) during the 4 s period.
Figure 7B:
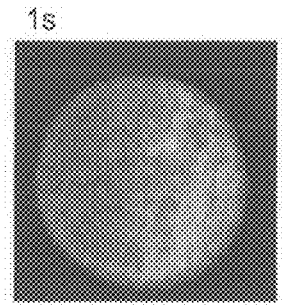
Figure 7C:
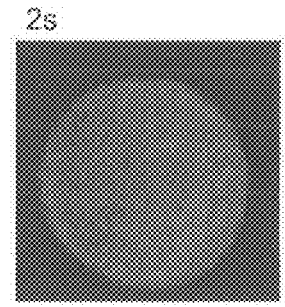
Figure 7D:
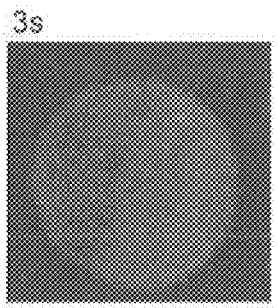
Figure 7E:
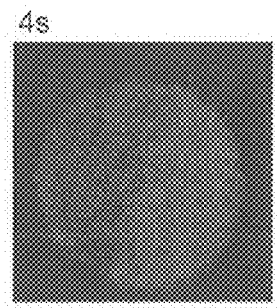
Figure 7F:
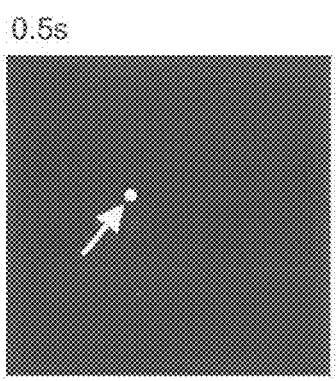
Figure 7G:
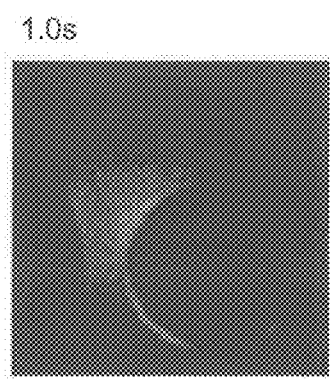
Figure 7H:
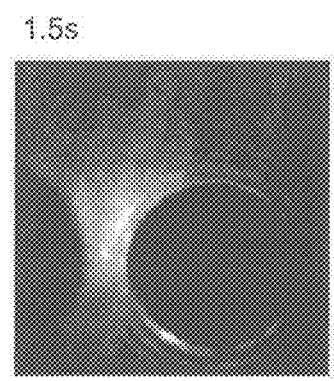
Figure 7I:
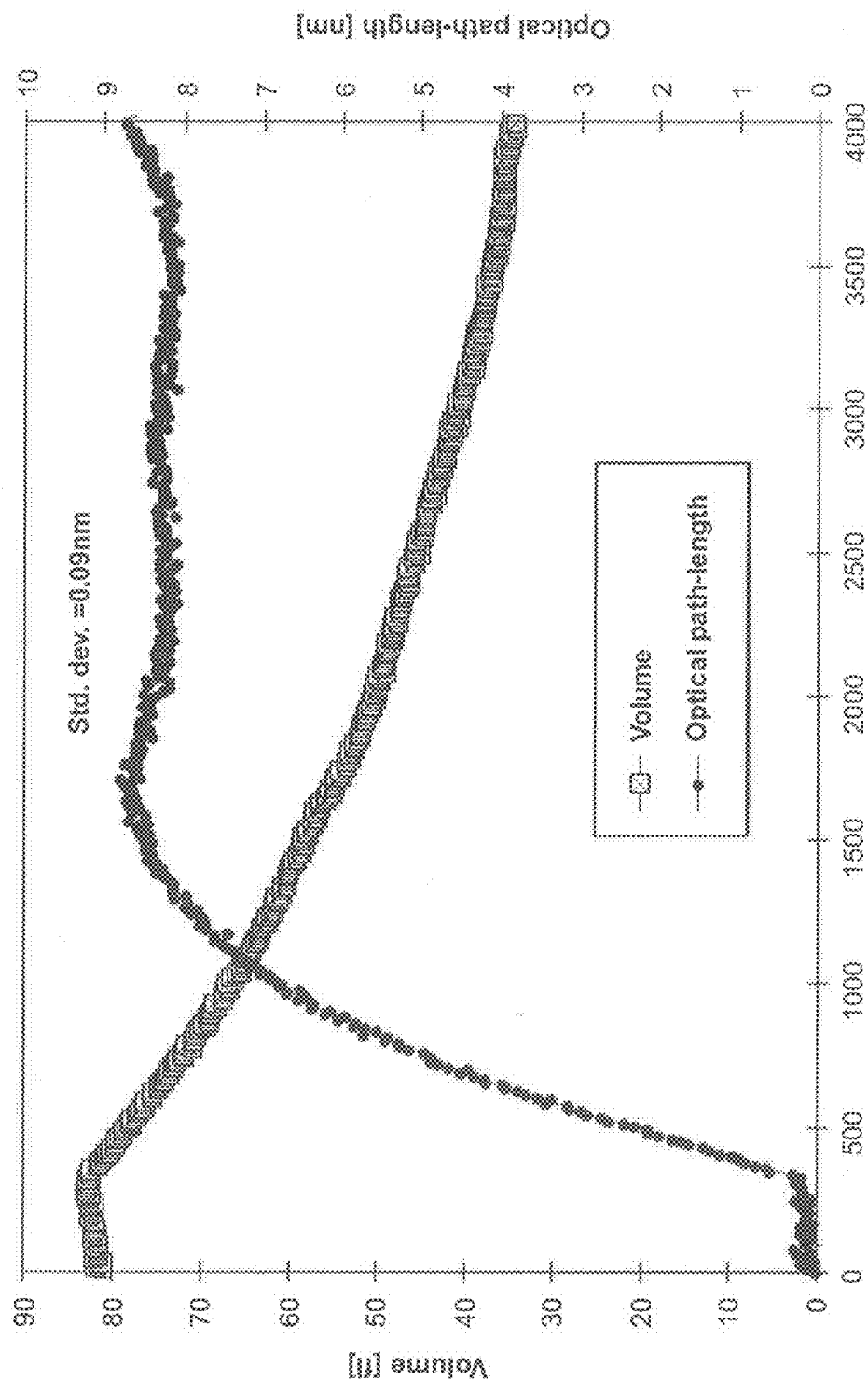

Hemolysis (RBC "lysing") is a phenomenon in which the erythrocyte membrane ruptures and the cell loses its hemoglobin content. This process has been studied recently in the context of optical clearing. Using the HPM instrument, a sequence of 1,000 phase images was used, at 10.3 milliseconds acquisition time, to dynamically quantify the changes in the cell as the result of spontaneous lysing. FIGS. 7a-7e depict the cell volume decrease during various stages of hemolysis. Note the unusual flat shape of the cell. The phase shifts owing to the expelled hemoglobin can be observed in FIGS. 7f-7h, where only the region surrounding the cell is represented, to avoid gray-scale saturation. The membrane rupture is highly localized, as indicated by the asymmetry in the FIGS. 7f-7h, and the hemoglobin appears to be diffusing from a point source on the cell. The RBC volume was evaluated during the process and its temporal dependence is plotted in FIG. 7i. During this highly dynamic process, the volume of the cell decreases by 50% in less than 4 seconds (the signal was averaged over 2 frames). On the other hand, the phase shift associated with a point in close proximity to the cell reaches a steady-state maximum level of almost 9 nm in about one second. In order to improve the signal to noise of this ultra-sensitive measurement, the signal was averaged in space over 11×11 pixels and in time over 10 frames. The resulting standard deviation of these data reached the remarkably low value of 0.09 nm. The measured phase shift is linearly proportional to the local concentration of hemoglobin; thus, the roughly constant path-length shift reached after about 1500 ms can be interpreted as the result of equilibrium between the generation of molecules from the cell and the diffusion process.

Figure 8:
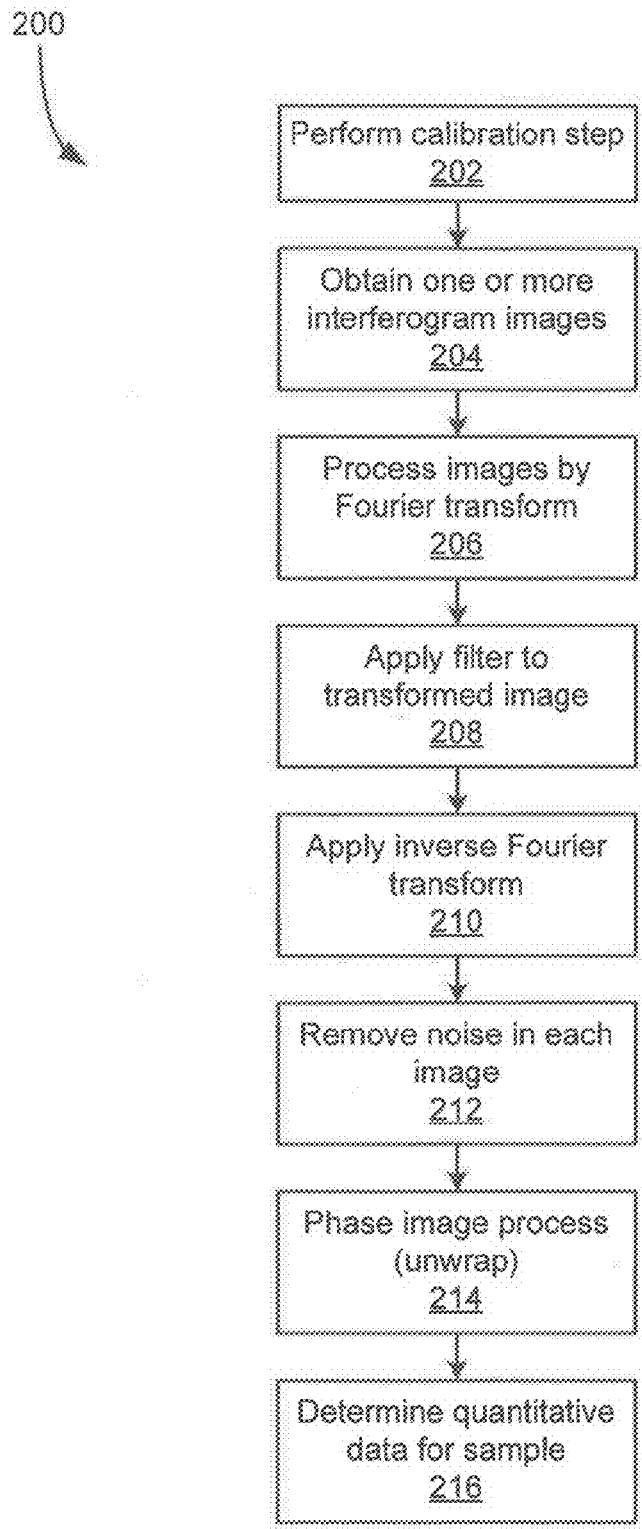
FIG. 8 is a process sequence used in a software program to process image data in accordance with a preferred embodiment of the invention.

A preferred method of performing Hilbert phase microscopy is shown in the process sequence 200 of FIG. 8. This process can be performed using a software program on a computer. First, a calibration step 202 can optionally be performed by obtaining an image of a known sample, which can then be used to remove background noise in the system. A sample to be measured is then mounted in a holder and one or more interferogram images of the sample are collected 204. A Fourier transform is then applied 206 to each image, following by filtering of the image 208. The inverse Fourier transform is then applied 210 followed by noise removal 212. A phase unwrapping step 214 and determination of other quantitative properties of the sample can then be obtained 216.

Preferred embodiments of the invention can include configurations of Hilbert phase imaging according to the invention in which the optical geometry is set up for transmissive and/or reflective mode.

The invention provides for non-biological applications as well as biological applications; for instance the invention can provide for studying the phase profile of an optical fiber and/or other transparent or semi-transparent objects or materials. Preferred embodiments of the invention may employ a laser or other coherent light source as part of the light source optics. Wavelength from the ultraviolet visible or infrared region of the electromagnetic spectrum can be used.

Advantages of the invention include the speed and simplicity of obtaining quantitative image data. The inverted Hilbert phase microscope is capable of measuring quantitative phase images of cells at the sub-nanometer and millisecond scales. The inverted geometry makes the new instrument particularly appealing for quantitative cell biology, such as, for example, without limitation, the non-contact characterization of erythrocyte membrane mechanics.

Biological structures such as living cells are predominantly transparent under bright field illumination. Phase contrast (PC) and differential interference contrast (DIC) microscopy have been used extensively to infer morphometric features of cells without the need for exogenous contrast agents. These techniques transfer the information encoded in the phase of the imaging field into the intensity distribution of the final image. Thus, the optical phase shift through a given sample can be regarded as a powerful endogenous contrast agent, as it contains information about both the thickness and refractive index of the sample. From this point of view, mature erythrocytes (red blood cells, or RBCs) represent a very particular type of structure in that they lack nuclei and major organelles. Thus, RBCs can be modeled as optically homogeneous objects, i.e., they produce local, optical, phase shifts that are proportional to their thickness. Therefore, measuring quantitative phase images of red blood cells provides cell thickness profiles with an accuracy that corresponds to a very small fraction of the optical wavelength. Such nanoscale topographic information provides insight into the biophysical properties and health state of the cell. Cells with nuclei or optically opaque components can be measured using the reflective process described earlier.

Further preferred embodiments according to the invention provide methods for quantifying rapid biological phenomena, such as millisecond scale RBC membrane fluctuations, using Hilbert phase microscopy (HPM) as a technique complementary to Fourier phase microscopy (FPM). HPM extends the concept of complex analytic signals to the spatial domain and measures quantitative phase images from only one spatial interferogram recording. Due to its single-shot nature, the HPM acquisition time is limited only by the recording device and thus can be used to accurately quantify nanometer level path-lengths shifts at the millisecond time scales or less, where many relevant biological phenomena develop. Images are preferably obtained in less than a one second time period and in most applications in less than 100 milliseconds. As a result, video recording of dynamic events can be recorded at the cellular level.

While the invention has been described in connection with specific methods and apparatus, it is to be understood that the description is by way of example of equivalent devices and methods and not as a limitation to the scope of the invention as set forth in the claims.

The invention claimed is:

1. A quantitative phase imaging device comprising:
    a light source that generates light transmitted along a first optical path and a second optical path, the light transmitted on the first optical path illuminating a full field of view of a sample;
    an imaging device positioned relative to the first optical path and the second optical path such that light from the sample positioned relative to the first optical path is detected by the imaging device and light from the second optical path is tilted at an angle relative to the light from the sample that is incident on the imaging device to provide an interference pattern, the imaging device generating image data of the sample;
    a processor that processes the image data with a Hilbert transform to provide a full field quantitative phase image of the sample.

2. The device of claim 1 further comprising a rotating mirror.

3. The device of claim 1 wherein the imaging device collects at least 10 frames per second.

4. The device of claim 1 wherein the processor performs the Hilbert transform on the image data.

5. The device of claim 1 wherein the device comprises an interferometer.

6. The device of claim 1 wherein the device comprises a microscope.

7. A method of imaging an object comprising:
    splitting light from a light source along a first optical path including an object to be imaged and a second reference optical path;
    combining light from the object along the first optical path and the second reference optical path with a combiner, the first optical path being tilted at an angle relative to the second optical path to form a fringe structure at a two-dimensional imaging device having a plurality of pixels;
    detecting a two dimensional image of the fringe structure with the two-dimensional imaging device; and
    processing the two dimensional image with a data processor configured to apply a Hilbert transform to obtain quantitative phase image data.

8. The method of claim 7 further comprising using a fiber optic device to couple light from the light source to the object.

9. The method of claim 7 wherein the second reference optical path couples a reference field light beam to the imaging device.

10. The method of claim 9 wherein the reference field beam is tilted at the angle with respect to a sample field beam transmitted through, or reflected by, the object.

11. The device of claim 1 further comprising performing a Fourier transform on the image data.

12. The device of claim 1 wherein the device comprises an inverted microscope.

13. The device of claim 1 further comprising a lens to receive light from the sample, a combiner to combine light from the lens that is tilted at an angle with light from the second optical path.

14. The device of claim 13 further comprising a lens between the combiner and the imaging device.

15. The method of claim 7 further comprising imaging a biological sample.

16. The method of claim 7 further comprising generating a plurality of images in sequence to image a dynamic process.

17. A method of imaging a dynamic biological process comprising:
    illuminating a biological material with light from a light source;
    detecting light from the biological material with a two dimensional imaging detector having a plurality of pixels to generate a plurality of images, the light from the biological material that is incident upon the imaging detector being combined with reference light that is tilted at an angle relative to the light from the biological material that is incident upon the detector form a fringe pattern; and
    processing the images with a data processor programmed to perform a Hilbert transform of each image to generate quantitative phase images of the biological material.

18. The method of claim 17 further comprising coupling the illuminating light to the biological material with a fiber optic device to generate the quantitative phase images.

19. The method of claim 17 wherein the light source and imaging detector comprises a microscope, the microscope displaying images on a display.

20. The method of claim 17 further comprising simultaneously illuminating a full field view of the biological material to generate at least 10 image frames per second of full field images of the biological material.

* * * * *